United States Patent
Carter et al.

[11] Patent Number: 5,935,128
[45] Date of Patent: Aug. 10, 1999

[54] ORTHOPAEDIC TEMPLATE SYSTEM INCLUDING A JOINT LOCATOR

[75] Inventors: Peter R. Carter, Dallas, Tex.; Gary T. Hamman, Warsaw, Ind.; Kenneth S. Jackson, Warsaw, Ind.; Mari S. Truman, Warsaw, Ind.; Randall N. Allard, Plymouth, Ind.

[73] Assignee: Bristol-Myers Squibb Co., New York, N.Y.

[21] Appl. No.: 08/844,155

[22] Filed: Apr. 18, 1997

[51] Int. Cl.⁶ .................................................. A61B 17/56
[52] U.S. Cl. ................................ 606/69; 606/88; 606/102
[58] Field of Search ................................ 606/87, 88, 89, 606/86, 96, 82, 69, 70, 71

[56] References Cited

U.S. PATENT DOCUMENTS

| | | |
|---|---|---|
| 4,565,191 | 1/1986 | Slocum . |
| 4,929,247 | 5/1990 | Rayhack . |
| 5,006,120 | 4/1991 | Carter . |
| 5,021,056 | 6/1991 | Hofmann et al. . |
| 5,042,983 | 8/1991 | Rayhack . |
| 5,049,149 | 9/1991 | Schmidt . |
| 5,053,039 | 10/1991 | Hofmann et al. . |
| 5,078,719 | 1/1992 | Schreiber . |
| 5,112,334 | 5/1992 | Alchermes et al. . |
| 5,147,364 | 9/1992 | Comparetto . |
| 5,176,685 | 1/1993 | Rayhack . |
| 5,254,119 | 10/1993 | Schreiber . |
| 5,364,402 | 11/1994 | Mumme et al. ........................... 606/88 |
| 5,413,579 | 5/1995 | Du Toit . |
| 5,470,335 | 11/1995 | Du Toit . |
| 5,540,695 | 7/1996 | Levy . |
| 5,569,260 | 10/1996 | Petersen ..................................... 606/88 |

FOREIGN PATENT DOCUMENTS

| | | |
|---|---|---|
| 340176 | 11/1989 | European Pat. Off. . |
| 380451 | 8/1990 | European Pat. Off. . |
| 466659 | 1/1992 | European Pat. Off. . |
| 538153 | 4/1993 | European Pat. Off. . |

OTHER PUBLICATIONS

Rayhack Osteotomy System™—Radial Shortening in Kienböck's Disease—Creative Medical Designs, Inc.—Sep. 1, 1995.

Rayhack Osteotomy Systems™—Rayhack Radial Distractor—Creative Medical Designs, Inc.—No date available.

"Biomechanics of Ulnar Osteotomies and Plate Fixation"—Rayhack et al—Clin & Lab Perform of Bone Plates—1994.

Forte Distal Radial Plate System—Zimmer, Inc.—c1994—Literature No. 97–2480–00.

Osteotomy System–The Complete Knee Solution—Zimmer, Inc.—c1994—Literature No. 97–5250–101.

ROS™ System—Rayhack Osteotomy System—Terray Corporation—No date available.

*Primary Examiner*—Guy V. Tucker
*Attorney, Agent, or Firm*—Margaret L. Geringer

[57] ABSTRACT

The invention is directed to an orthopaedic template system for use with a bone (14) having a shaft and a bearing surface at an end of the shaft. A first template (30) is attachable to the bone end adjacent to the bearing surface, and includes a first saw guide surface or slot (40). A joint locator (10) is used to position the first template (30) relative to the bearing surface. A second template (50) is pivotally attachable to the first template (30), whereby the second template (50) may be selectively positioned at one of a plurality of angular orientations relative to the first template. A third template (70) includes a second saw guide surface or slot (78), and is attachable to the first template (30) at a plurality of locations (72, 74, 76), whereby the second saw guide slot (78) may be selectively positioned relative to the first saw guide slot (40).

34 Claims, 4 Drawing Sheets

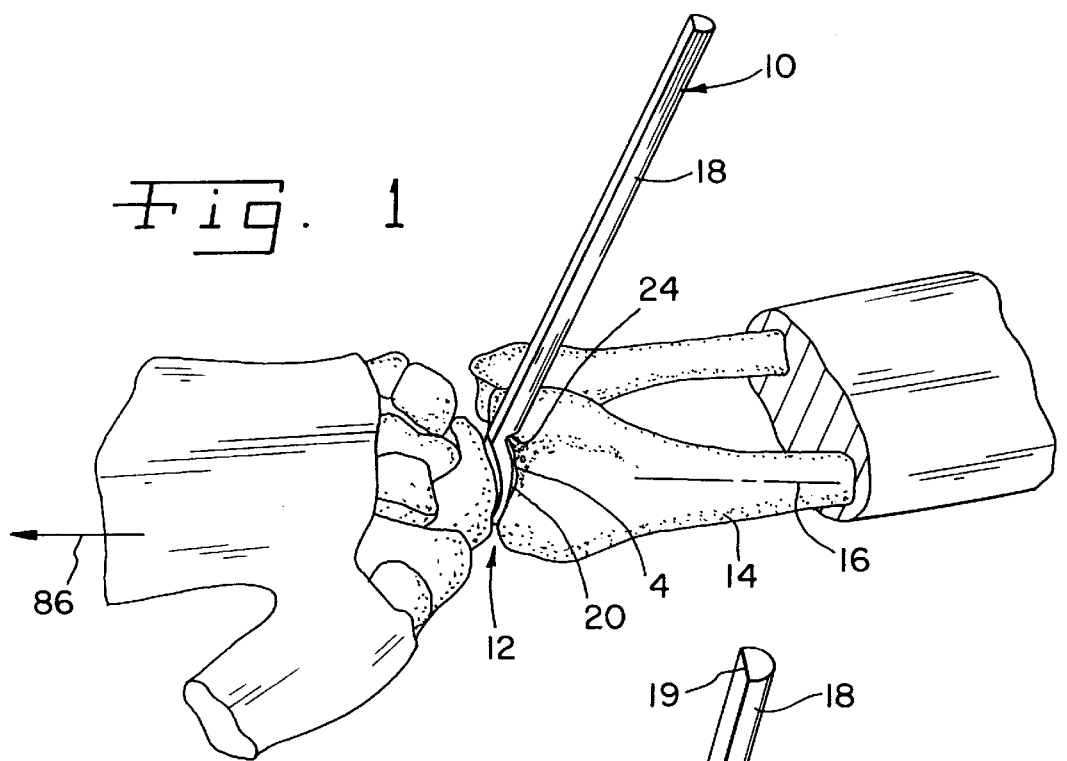
Fig. 1
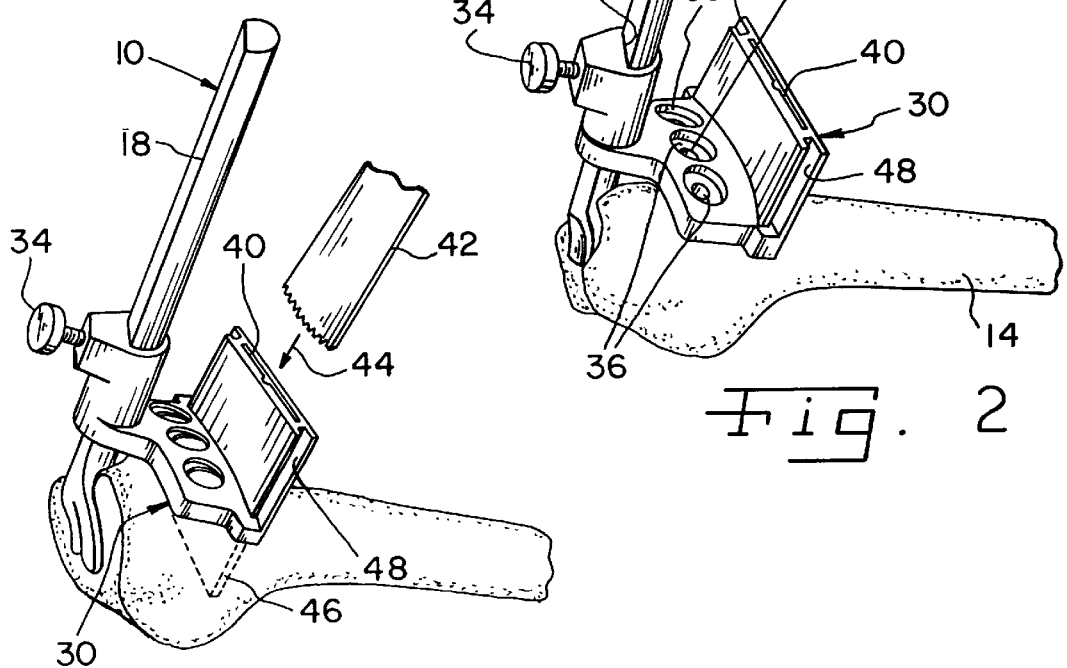
Fig. 2
Fig. 3

ORTHOPAEDIC TEMPLATE SYSTEM INCLUDING A JOINT LOCATOR

BACKGROUND OF THE INVENTION

1. Field of the Invention

The present invention relates to orthopaedic instrumentation, and, more particularly, to orthopaedic instrumentation for use in association with a bearing surface at an end of a bone.

2. Description of the Related Art

Orthopaedic surgery on a radius may be necessary for a number of different reasons. For example, the distal end of the radius may become fractured and require the use of a fixating plate to maintain the radius during the healing process. Another type of orthopaedic surgery on a distal radius may be to correct an angular orientation of the bearing surface relative to the longitudinal axis of the bone. It is known to cut the end of the radius using a free-hand technique, and a wedge shaped bone graft is placed within the resulting opening and the bone secured by a bone plate.

It is also known to perform an orthopaedic procedure on the distal end of a radius to shorten the length of the radius and thereby reduce the forces which are exerted on associated soft tissue. Similar to a conventional angular correction procedure, it is also known to remove a small portion of bone toward a distal end of the radius using a free-hand technique, and then securing the bone portions with a bone plate.

In addition, examples of orthopaedic devices which may be used during orthopaedic surgery at the distal end of a radius are disclosed, e.g., in U.S. Pat. No. 5,006,120 (Carter); U.S. Pat. Nos. 5,176,685; 5,042,983; 4,929,247 (Rayhack), and a surgical technique brochure for a Rayhack Osteotomy system entitled "Radial Shortening in Keinböck's Disease," published by Creative Medical Designs, Inc.

What is needed in the art is an orthopaedic system which utilizes accurate instrumentation for providing more predictable results which allows either an angular correction procedure or a radial shortening procedure to be carried out which may use at least some common instrumentation, thereby reducing the complexity and cost of associated separate systems. Such a system would be beneficial for use with a low profile radius plate, such as the Forte Distal Radius Plate sold by Zimmer, Inc. which is specifically designed for this bone's dorsal subtendenous surface.

SUMMARY OF THE INVENTION

The present invention provides a template system including a joint locator which is used to position a first template relative to an end of a bone and adjacent to a bearing surface. The first template is attachable to a second template for angular correction, or to a third template for radial shortening.

The invention comprises, in one form thereof, an orthopaedic template system for use with a bone having a shaft and a bearing surface at an end of the shaft. A first template, which may be a T-template, is attachable to the bone end adjacent to the bearing surface, and includes a first saw guide surface or slot. A second template is pivotally attachable to the first template, whereby the second template may be selectively positioned at one of a plurality of angular orientations relative to the first template. A third template includes a second saw guide surface or slot, and is attachable to the first template at a plurality of locations, whereby the second saw guide surface or slot may be selectively positioned relative to the first saw guide surface or slot.

The invention comprises, in another form thereof, an orthopaedic instrument for use in association with a bearing surface on a bone which is oriented relative to a longitudinal axis of a bone. The instrument includes a joint locator having a handle and a bone engaging end attached to and extending from the handle. The bone engaging end is configured to engage the bearing surface such that the handle is disposed at a corresponding orientation relative to the longitudinal axis and thereby provides an indication of the orientation of the bearing surface relative to the longitudinal axis.

An advantage of the present invention is that the first template is attachable with either an angular correction template or a radial shortening template.

Another advantage is that the first template is positioned adjacent the bearing surface using a joint locator engaged with the bearing surface.

Yet another advantage is that the joint locator provides a visual indication of the orientation of the bearing surface.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a fragmentary, perspective view of a wrist with an embodiment of a joint locator of the present invention engaged therewith;

FIG. 2 is a perspective view of the radius shown in FIG. 1, with the joint locator being attached to a T-template;

FIG. 3 is a perspective view of the joint locator and T-template shown in FIG. 2, and a saw blade positioned in association with a saw guide slot in the T-template;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 4A:
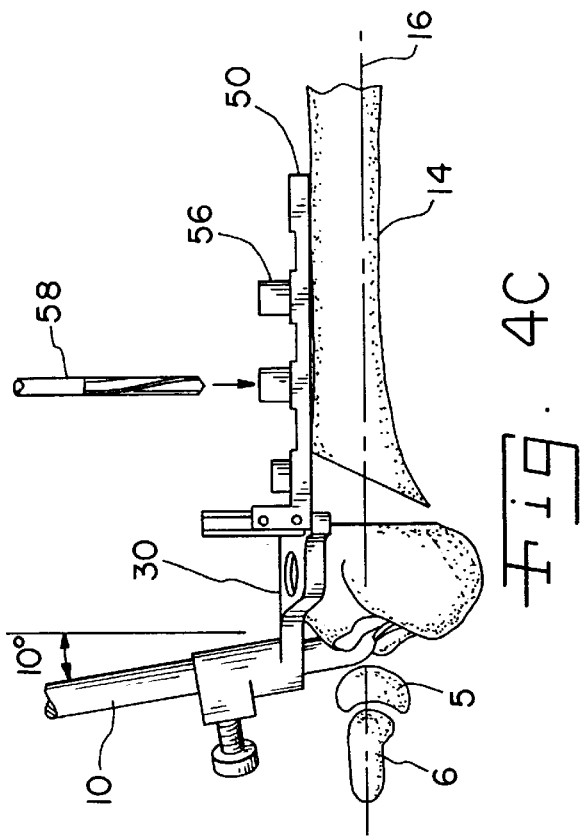
FIG. 4A is a side view of the joint locator and T-template shown in FIG. 3, with an angular correction template being pivotally attached to the T-template after the saw cut has been made and prior to any angular correction.

Referring now to the drawings, an embodiment of an orthopaedic template system, including a joint locator, will be described in further detail.

It is noted that the Figs. show instrumentation adapted for use on a right wrist. It may be beneficial for certain of the instruments, such as the joint locator 10 and the first template 30 to be designed for use on a right wrist, with the corresponding instrument for a left wrist being a mirror image thereof.

Figure 10:
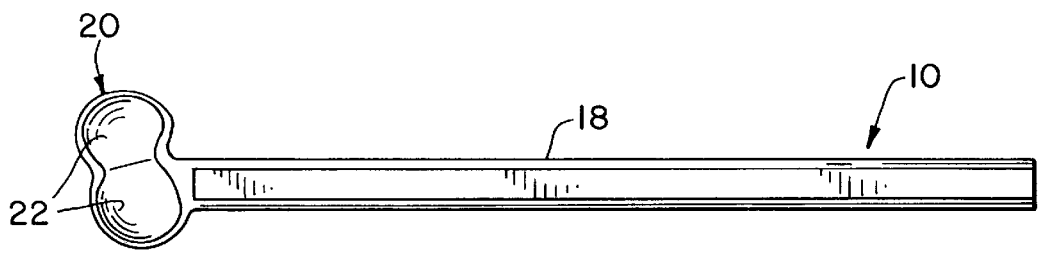
FIG. 10 is an elevational view of the joint locator shown in FIGS. 1–3, 4A,B,C,D and 6.
Figure 11:
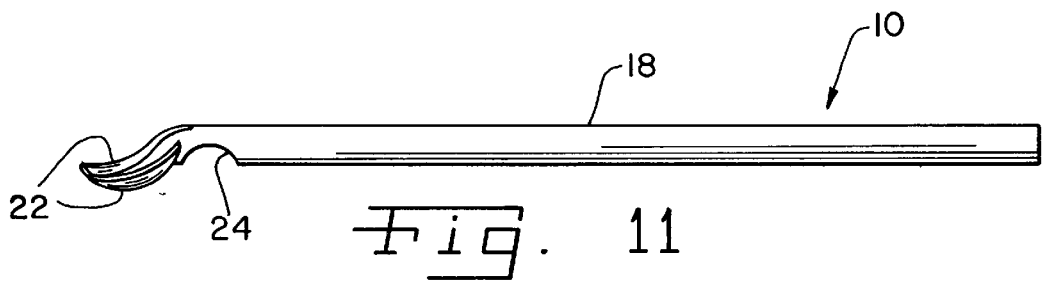
FIG. 11 is a side view of the joint locator shown in FIG. 10.

Referring more specifically to FIG. 1, there is shown a fragmentary, perspective view of an embodiment of a joint locator 10 which is inserted into a joint space 12 in a wrist at an end of a radius 14. The radius 14 includes a bearing surface 4 at the end thereof having a general orientation relative to a longitudinal axis 16 of radius 14. Joint locator 10 includes a handle 18 and a bone engaging end 20 which is attached to and extends from handle 18 (shown in greater detail in FIGS. 10 and 11). Bone engaging end 20 is configured to engage the bearing surface 4 of radius 14 such that handle 18 is disposed at a corresponding orientation relative to the longitudinal axis 16, and thereby provides an indication of the orientation of the bearing surface relative to longitudinal axis 16. In the embodiment shown, bone engaging end 20 is in the form of two condyle shaped portions 22 each having a convex shape on one side which corresponds to the shape of the bearing surface on radius 14 for engagement therewith, and an oppositely located concave surface which corresponds to the shape of the mating carpus area bones. A notch 24 is formed in handle 18 relatively closely adjacent to condyle shaped portions 22. Notch 24 is configured to engage radius 14 at a location on a periphery or rim of the bearing surface 4 of radius 14. When condyle shaped portions 22 are engaged with the bearing surface 4 and notch 24 is engaged with the rim of the bearing surface, handle 18 provides a visual indication of the general orientation of the bearing surface relative to longitudinal axis 16.

Referring now to FIG. 2, joint locator 10 is shown being attached to a first template or T-template 30. T-template 30 includes an opening 32 for slidingly receiving joint locator 10. A thumbscrew 34 associated with opening 32 is threadingly engaged with T-template 30 and locks joint locator 10 within opening 32. T-template 30 and joint locator 10 thus coact with each other to position T-template 30 adjacent to the bearing surface at the end of radius 14. The locator handle 18 may include a flat surface 19 which cooperates with flat surface 33 of opening 32. The flat surfaces 19 and 33 are oriented relative the condyle shaped portion 22 which engages the bearing surface of the radius 14 to provide proper orientation of T-template 30 to the bearing surface 4. The bearing surface 4 provides a landmark on which the proper radial corrections can be made. The handle 18 of locator 10 provides a lever for helping to control the position of the distal portion of the radius 14. T-template 30 also includes at least one hole 36 therein, and preferably includes three holes 36 as shown in FIGS. 2 and 3. T-template 30 is attached to the end of radius 14 using a plurality of fasteners or screws 38 which are received in respective holes 36. At a minimum, at least one screw 38 is used to attach T-template 30 to radius 14.

Figure 7:
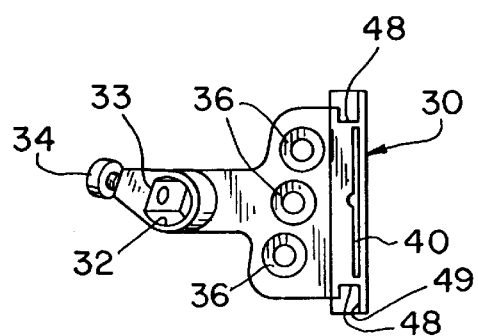
FIG. 7 is a top view of the T-template shown in FIG. 2.

T-template 30 also includes a saw guide surface or slot 40 (FIGS. 2, 3 and 7) which is sized and configured for receiving a saw blade 42 therein. Saw blade 42 is inserted into saw guide slot 40 (as indicated by directional arrow 44 in FIG. 3), and guides saw blade 42 through radius 14 (indicated by dashed lines 46 in FIG. 3). T-template 30 also includes a pair of locating surfaces or slots 48 which are configured for attachment with other templates, as will be described in greater detail hereinafter.

Figure 4C:
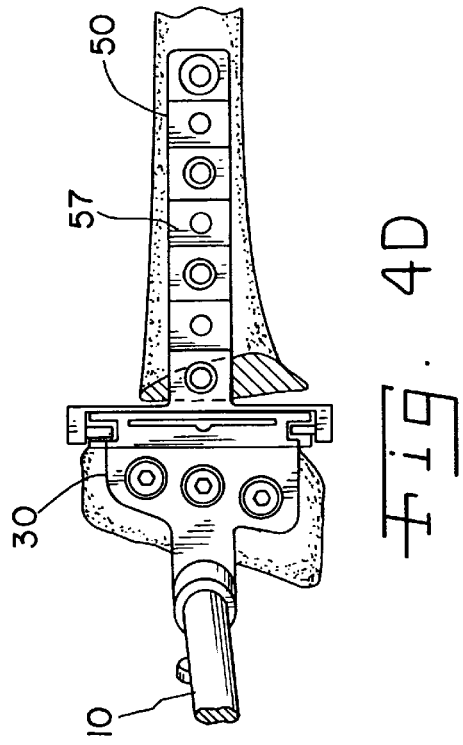
FIG. 4C is a side view of the instrumentation of FIG. 4A after angular correction has been made and with a drill positioned above a drill guide in the angular correction template.
Figure 4B:
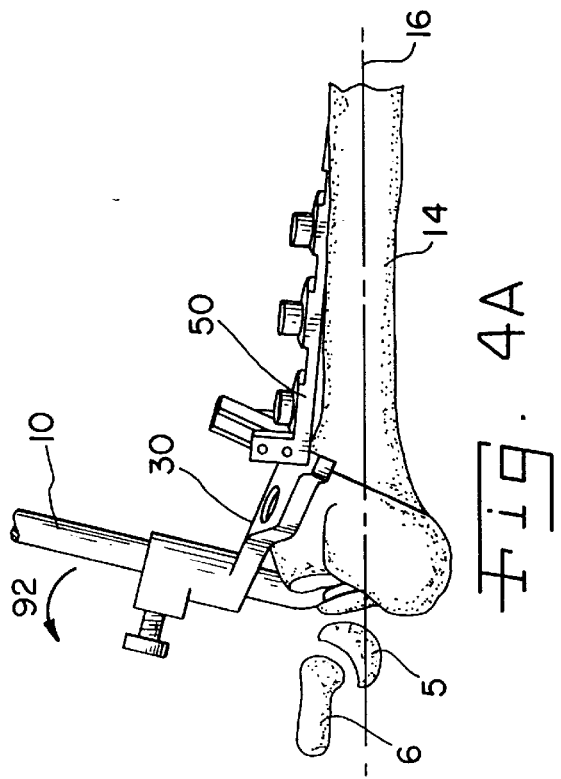
FIG. 4B is a top view of the instrumentation of FIG. 4A.
Figure 4D:
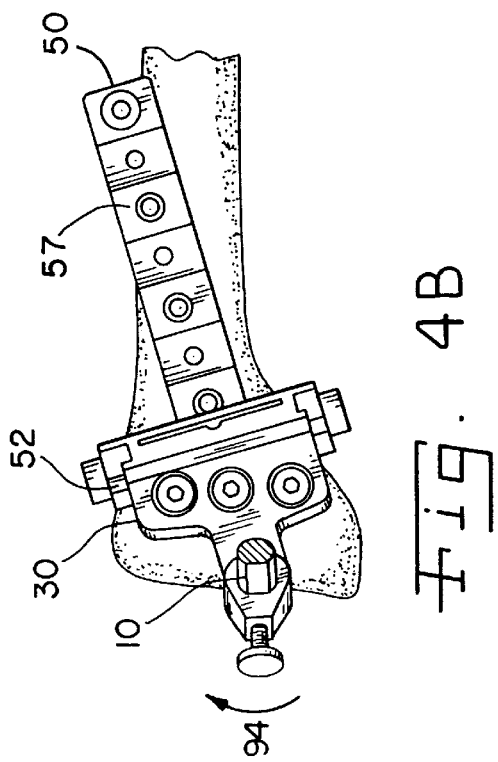
FIG. 4D is a top view of the instrumentation of FIG. 4C.
Figure 5:
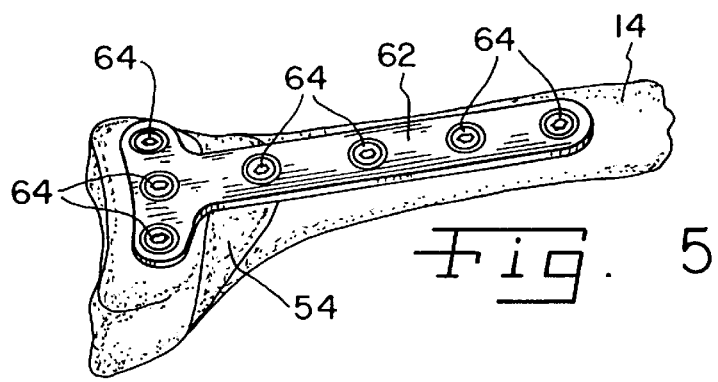
FIG. 5 is a perspective view of the fixating plate attached to the radius shown in FIGS. 4C and D, after use of the T-template and angular correction template.
Figure 8:
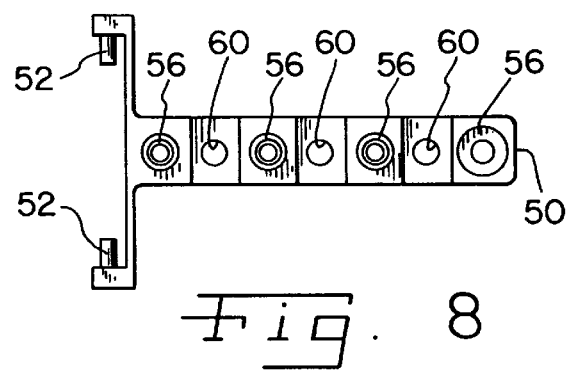
FIG. 8 is a top view of the angular correction template shown in FIGS. 4A,B,C, and D.
Figure 8A:
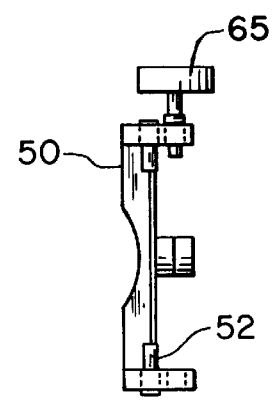
FIG. 8A is a front view of the angular correction template shown in FIG. 8 with an additional locking screw shown.

Referring now to FIGS. 4A,B,C, and D, and 8, conjunctively, an embodiment of a second or angular correction (AC) template 50 is shown. AC template 50 is pivotally attached to T-template 30, whereby AC template 50 may be selectively positioned at one of a plurality of angular orientations relative to T-template 30 and is adjustably positioned to accommodate the radial deformity. More particularly, AC template 50 includes a pair of projections or pins 52 which are slidingly received along or within respective locating surfaces or slots 48 of T-template 30. Pins 52 may slide within locating slots 48 and allow pivotal movement between AC template 50 and T-template 30. When the end of radius 14 is cut, an angular correction of the bearing surface 4 can be made, such as shown in FIGS. 4C and 4D. AC template 50 accommodates the changing angular orientation between the bearing surface 4 and the longitudinal axis of radius 14, thus allowing the AC template 50 to adjust to the proper position relative to the angularly corrected radius of FIGS. 4C and 4D. A thumbscrew 65 shown in FIG. 8A, may be provided on AC template 50 to engage slot 48 to secure the position of AC template 50 relative to first template 30, if desired. A second thumbscrew (not shown) may also be provided to engage the oppositely located slot 48, if desired. AC template 50 also includes a plurality of drill guides 56 for guiding a drill 58 after the angular correction of radius 14 has been made. A plurality of holes 60 in AC template 50 accommodate a clamp (not shown) which is used to clamp AC template 50 to radius 14 during a drilling operation with drill 58. The holes which are formed in radius 14 through holes 36 in T-template 30 and through drill guides 56 in AC template 50 correspond to the hole pattern in a fixating plate 62 (FIG. 5) which is attached to radius 14 using a plurality of screws 64.

Figure 6:
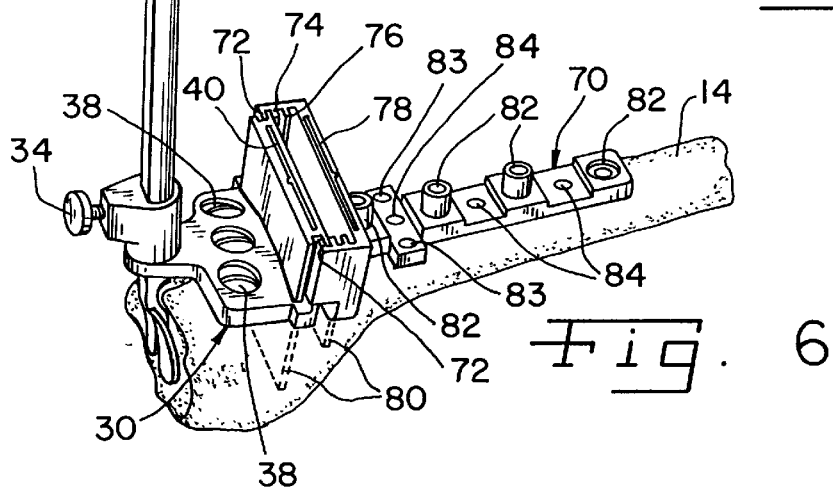
FIG. 6 is a perspective view of the joint locator and T-template shown in FIG. 2, with a radial shortening template attached to the T-template.
Figure 9:
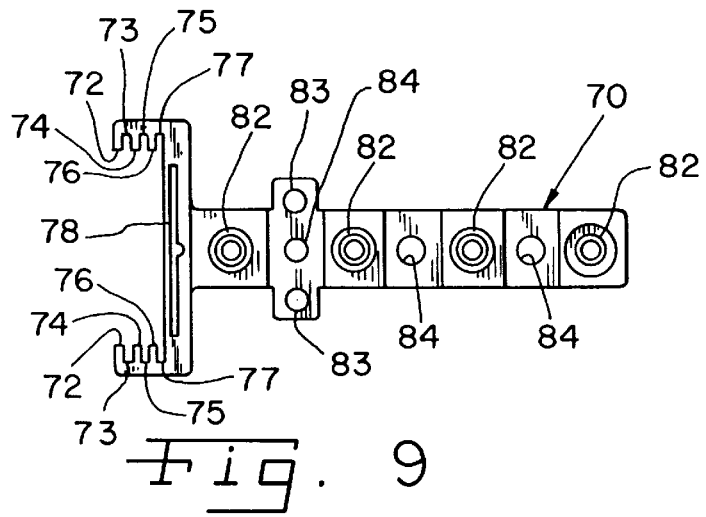
FIG. 9 is a top view of the radial shortening template shown in FIG. 6.

Referring now to FIGS. 6 and 9, conjunctively, a third or radial shortening (RS) template 70 is shown in attachment with T-template 30. RS template 70 includes a plurality of opposing pairs of projections 72, 74 and 76 which are slidingly received along or within respective locating surfaces or slots 48 of T-template 30. RS template 70 also includes a second saw guide surface or slot 78 which is disposed in substantially parallel relationship to saw guide slot 40 when RS template is attached with T-template 30. Opposing pairs of projections 72, 74 and 76, which form slots 73,75,77, allow RS template 70 to be attached to T-template 30 at a plurality of locations, whereby saw guide slot 78 may be selectively positioned relative to saw guide slot 40. First saw guide slot 40 and second saw guide slot 78 guide a saw blade (such as shown in FIG. 3) through radius 14 (as indicated by dashed lines 80 in FIG. 6). RS template 70 also includes a plurality of drill guides 82 for guiding a drill into radius 14 (such as drill 58 shown in FIG. 4C), and a plurality of holes 84 providing interconnection with a clamp (not shown) used to clamp RS template 70 to radius 14. Side drill guide holes 83 are provided for drilling holes in bone for subsequent use with a bone clamp (not shown) to draw bone fragments together.

In use, for either the angular correction or radial shortening procedure, an incision is made at the wrist and the joint space is distracted as indicated by arrow 86. Joint locator 10 is inserted into joint space 12 such that the convex condyle shaped portions 22 engage the bearing surface 4 at the end of radius 14. Notch 24 provides clearance around the periphery of the bearing surface and is engaged with the periphery of the bearing surface. Handle 18 provides a visual indication of the orientation of the bearing surface relative to the longitudinal axis 16 of radius 14. T-template 30 is then engaged with joint locator 10 such that handle 18 is received within opening 32 and locked into place using thumbscrew 34. At least one screw 38 is then inserted through a corresponding hole 36 in T-template 30 and into radius 14 to attach T-template 30 at the end of radius 14 adjacent to the bearing surface. If an angular correction procedure is to be followed, a saw blade 42 is inserted into saw guide slot 40 and through radius 14. AC template 50 is then attached to T-template 30, such that pins 52 are received within locating slots 48 as shown in FIGS. 4A and 4B. The distal end of the cut radius 14 is rotated (in the direction of arrow 92 of FIG. 4A) to restore the proper volar tilt of approximately 10° as shown in FIG. 4C. The 10° volar tilt is angled distally relative to a line which is perpendicular to the longitudinal axis of radius 14. If the elongated portion 57 of AC template 50 is not aligned with the longitudinal axis 16 of the radius 14 in the top view, such as shown in FIG. 4B, the distal end of the cut radius is also rotated (for example, in the direction of arrow 94 of FIG. 4B) to align elongated portion 57 of AC template 50 with the axis 16 of radius 14 as shown in FIG. 4D. This provides a radial correction in addition to the volar correction previously described. Aligning the elongated portion 57 to the axis 16 of radius 14 provides the proper radial correction. Ultimately, the amount of angular correction is determined by the judgment of the surgeon. Once the desired volar and radial angular corrections are obtained, at least one clamp (not shown) is engaged to a hole 60 in AC template 50 to clamp AC template 50 to radius 14, thus stabilizing the proper alignment of the bones. It is noted that upon securing the proper angular orientation of the bearing surface of the radius, the wrist will become properly aligned in all planes as evidenced by the proper alignment of the lunate bone 5 and capitate bone 6 with the radius 14, as shown in FIG. 4C. A drill 58 is then inserted through drill guides 56 to form holes in radius 14 at particular locations corresponding to the pattern of the fixating plate 62. Joint locator 10, T-template 30 and AC template 50 are then removed, and the bone graft 54 is placed into the resulting wedge shaped opening. A fixating plate 62 is then attached to the radius by screws 64 utilizing the preformed holes therein. Any voids under the plate may be filled with bone graft, as appropriate.

On the other hand, if a radial shortening procedure is to be followed, an RS template 70, as shown in FIGS. 6 and 9, is slidingly engaged with and attached to T-template 30 at a particular location such that the second saw guide slot 78 in RS template 70 is disposed a predetermined distance away from the first saw guide slot 40 in T-template 30. The cuts are made in the radius through saw guide slots 40, 78, and the resulting free-floating piece of bone is removed. The thickness of bone removed is determined by which slot 73,75, or 77 is selected. RS template 70 is clamped in place using at least one clamp (not shown) which engages one of the holes 84. Holes are formed in radius 14 by inserting a drill 58 through a plurality of drill guides 82 in RS template 70. Joint locator 10, T-template 30 and RS template 70 are then removed, the cut bone portions brought together, and a fixating plate with a corresponding hole pattern is attached to radius 14.

Figure 9A:
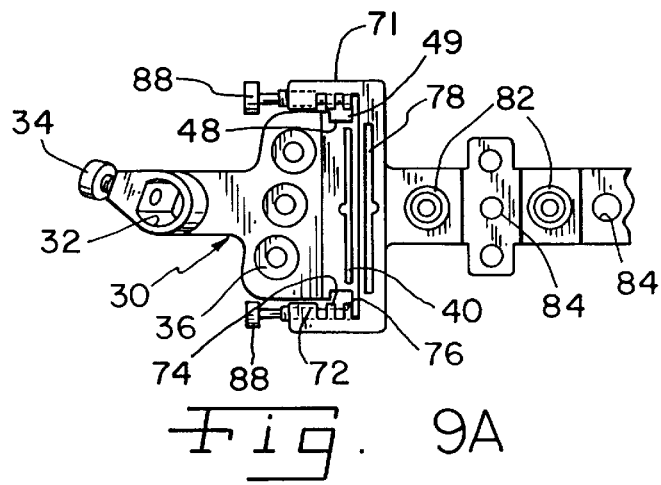
FIG. 9A is a top view of an alternate radial shortening template which includes additional securing screws.

An alternate RS template 71 is shown in FIG. 9A which provides a means of rigidly fixing the RS template 71 to T-template 30. Thumbscrews 88 are provided which threadingly engage the RS template 71 to secure the locating surface 49 of locating slot 48 in the desired slot of RS template 71.

The T-template, AC template, RS template and joint locator are preferably made of stainless steel, although any suitable material may be used. These components may be provided in various sizes as desired.

While this invention has been described as having a preferred design, the present invention can be further modified within the spirit and scope of this disclosure. For example, the features of the present invention can be adapted for use on other bones, as appropriate. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrument system adapted for use with a bone, the bone having a shaft and a bearing surface at an end of the shaft, said instrument system comprising:

a first template adapted for attachment to the bone end adjacent to the bearing surface, said first template including a first saw guide surface;

a second template which is pivotally attachable to said first template, whereby said second template may be selectively positioned at one of a plurality of angular orientations relative to said first template; and a third template including a second saw guide surface, said third template attachable to said first template at a plurality of locations, whereby said second saw guide surface may be selectively positioned relative to said first saw guide surface.

2. The orthopaedic instrument system of claim 1, further comprising a joint locator which is attachable with said first template and adapted for engagement with the bearing surface, said joint locator providing an indication of an orientation of the bearing surface.

3. The orthopaedic instrument system of claim 2, wherein said first template includes an opening for slidingly receiving said joint locator, and wherein said first template further includes a thumbscrew associated with said opening for locking said joint locator within said opening.

4. The orthopaedic instrument system of claim 1, wherein said first template includes a pair of locating slots, and wherein said second and third templates each include a pair of projections which may be slidingly received in said respective locating slots.

5. The orthopaedic instrument system of claim 4, wherein said projections on said second template comprise pins.

6. The orthopaedic instrument system of claim 4, wherein said first and second saw guide surfaces are slots.

7. An orthopaedic instrument system adapted for use with a bone, the bone having a shaft and a bearing surface at an end of the shaft, said instrument system comprising:

a first template adapted for attachment to the bone end adjacent to the bearing surface;

a second template attachable with said first template, wherein said second template comprises an angular correction template; and a third template attachable with said first template.

8. An orthopaedic instrument system adapted for use with a bone, the bone having a shaft and a bearing surface at an end of the shaft, said instrument system comprising:

a first template adapted for attachment to the bone end adjacent to the bearing surface;

a second template attachable with said first template; and a third template attachable with said first template, wherein said third template comprises a radial shortening template.

9. An orthopaedic instrument system adapted for use with a bone, the bone having a shaft and a bearing surface at an end of the shaft. said instrument system comprising:

a first template adapted for attachment to the bone end adjacent to the bearing surface;

a second template attachable with said first template; and a third template attachable with said first template, wherein said second template comprises an angular correction template, and wherein said third template comprises a radial shortening template.

10. An orthopaedic instrument system adapted for use with a bone, the bone having a shaft and a bearing surface at an end of the shaft. said instrument system comprising:

a first template adapted for attachment to the bone end adjacent to the bearing surface;

a second template attachable with said first template; and a third template attachable with said first template, wherein said first template includes a first saw guide surface, and wherein said second template is pivotally attachable with said first template, and wherein said third template includes a second saw guide surface.

11. The orthopaedic instrument system of claim 10, wherein said third template is attachable with said first template at a plurality of locations such that said second saw guide surface may be selectively positioned relative to said first saw guide surface.

12. An orthopaedic instrument adapted for use in association with a bearing surface on a bone, the bearing surface being oriented relative to a longitudinal axis of the bone, said instrument comprising a joint locator having a handle and a bone engaging end attached to and extending from said handle, said bone engaging end being configured and adapted to engage said bearing surface such that said handle is disposed at a corresponding orientation relative to the longitudinal axis and thereby provides an indication of the orientation of the bearing surface relative to the longitudinal axis, and wherein said bone engaging end includes at least one condyle shaped portion which includes a convexly curved bone contacting surface corresponding to a shape of the bearing surface, and wherein said convexly curved bone contacting surface extends longitudinally from said handle.

13. The orthopaedic instrument of claim 12, wherein said bone engaging end includes two condyle shaped portions each including a convexly curved bone contacting surface.

14. The orthopaedic instrument of claim 12, wherein said handle includes a notch which is configured and adapted to engage the bone at a location on a periphery of the bearing surface.

15. The orthopaedic instrument of claim 12, further comprising a template which is adapted for attachment to the bone adjacent to the bearing surface, said template including an opening for receiving said handle therein.

16. The orthopaedic instrument of claim 15, wherein said template includes at least one hole therein, each said hole being sized to receive a corresponding fastener therein adapted for attaching said template to the bone.

17. The orthopaedic instrument of claim 15, wherein said template includes a saw guide surface.

18. An orthopaedic instrument system adapted for use with a bone, the bone having a shaft, said instrument system comprising:

a first template adapted for attachment to the bone, said first template including a first saw guide surface, and a second template which is pivotally attachable to said first template, whereby said second template may be selectively positioned at one of a plurality of angular orientations relative to said first template, said system further comprising a joint locator which is attachable with said first template and which includes a bone engaging end adapted for engagement with a bearing surface at an end of the bone shaft, and wherein said bone engaging end includes at least one condyle shaped portion which includes a curved contour corresponding to a shape of the bearing surface, said joint locator providing an indication of an orientation of the bearing surface.

19. An orthopaedic instrument system adapted for use with a bone, the bone having a shaft, said instrument system comprising:

a first template adapted for attachment to the bone, said first template including a first saw guide surface, a second template which is pivotally attachable to said first template, whereby said second template may be selectively positioned at one of a plurality of angular orientations relative to said first template, and a joint locator which is attachable with said first template and adapted for engagement with a bearing surface at an end of the bone shaft, said joint locator providing an indication of an orientation of the bearing surface, wherein said first template includes an opening for slidingly receiving said joint locator, and wherein said first template further includes a thumbscrew associated with said opening for locking said joint locator within said opening.

20. An orthopaedic instrument system adapted for use with a bone, the bone having a shaft, said instrument system comprising:

a first template adapted for attachment to the bone, said first template including a first saw guide surface, and a second template which is pivotally attachable to said first template, whereby said second template may be selectively positioned at one of a plurality of angular orientations relative to said first template, wherein said first template includes a pair of locating surfaces, and wherein said second template includes a pair of projections which may be slidingly received along said locating surfaces.

21. The orthopaedic instrument system of claim 20, wherein said projections on said second template comprise pins.

22. In combination, an orthopaedic instrument system and a corresponding bone fixation plate having bone plate holes therein and adapted for use with a bone, the bone having a shaft, said instrument system comprising:

a first template adapted for attachment to the bone, said first template including a first saw guide surface, and a second template which is pivotally attachable to said first template, whereby said second template may be selectively positioned at one of a plurality of angular orientations relative to said first template, wherein said second template includes drill guide holes adapted for use in forming holes in said bone, wherein the drill guide holes are positioned to align with said bone plate holes in said corresponding bone fixation plate.

23. The orthopaedic instrument system of claim 22, wherein said second template comprises an angular correction template.

24. An orthopaedic instrument system adapted for use with a bone, the bone having a shaft, said instrument system comprising:
- a first template adapted for attachment to the bone, said first template including a first saw guide surface, and
- a second template which is pivotally attachable to said first template, whereby said second template may be selectively positioned at one of a plurality of angular orientations relative to said first template, wherein said second template includes a clamp receiving locator portion adapted to secure the second template to said bone.

25. An orthopaedic instrument system adapted for use with a bone, the bone having a shaft, said instrument system comprising:
- a first template adapted for attachment to the bone, said first template including a first saw guide surface; and
- a further template including a second saw guide surface, said further template attachable to said first template at a plurality of locations, whereby said second saw guide surface may be selectively positioned relative to said first saw guide surface, said system further comprising a joint locator which is attachable with said first template and which joint locator includes a handle and a bone engaging end extending from said handle, said bone engaging end adapted for engagement with a bearing surface at an end of the bone shaft, and wherein said bone engaging end includes at least one condyle shaped portion which includes a convexly curved bone contacting surface corresponding to a shape of the bearing surface, and wherein said convexly curved bone contacting surface extends longitudinally from said handle, said joint locator providing an indication of an orientation of the bearing surface.

26. The orthopaedic instrument system of claim 25, wherein said first template includes an opening for slidingly receiving said joint locator, and wherein said first template further includes a thumbscrew associated with said opening for locking said joint locator within said opening.

27. In combination, an orthopaedic instrument system and a corresponding bone fixation plate having bone plate holes therein and adapted for use with a bone, the bone having a shaft, said instrument system comprising:
- a first template adapted for attachment to the bone, said first template including a first saw guide surface; and
- a further template including a second saw guide surface, said further template attachable to said first template at a plurality of locations, whereby said second saw guide surface may be selectively positioned relative to said first saw guide surface, wherein said further template includes drill guide holes adapted for use in forming holes in said bone, wherein the drill guide holes are positioned to align with said bone plate holes in said corresponding bone fixation plate.

28. The orthopaedic instrument system of claim 27, wherein said further template includes a clamp receiving locator portion adapted to secure the further template to said bone.

29. An orthopaedic instrument system adapted for use with a bone, the bone having a shaft, said instrument system comprising:
- a first template adapted for attachment to the bone, said first template including a first saw guide surface; and
- a further template including a second saw guide surface, said further template attachable to said first template at a plurality of locations, whereby said second saw guide surface may be selectively positioned relative to said first saw guide surface, wherein said first template includes a pair of locating surfaces, and wherein said further template includes a pair of projections which may be slidingly received along said locating surfaces, and wherein said further template includes a plurality of pairs of projections, such that any one of said plurality of pairs of projections can be selectively slidingly received along said locating surfaces to selectively adjust the relative position of the first and second saw guide surfaces.

30. An orthopaedic instrument system adapted for use with a bone, the bone having a shaft, said instrument system comprising:
- a first template adapted for attachment to the bone, said first template including a first saw guide surface; and
- a further template including a second saw guide surface, said further template attachable to said first template at a plurality of locations, whereby said second saw guide surface may be selectively positioned relative to said first saw guide surface, and wherein said further template comprises a radial shortening template.

31. An orthopaedic instrument system adapted for use with a bone, the bone having a shaft and a bearing surface at an end of the shaft, said instrument system comprising:
- a template adapted for attachment to the bone end adjacent to the bearing surface, said first template including a guide adapted for cutting bone; and
- a joint locator which is attachable with said template and which joint locator includes a handle and a bone engaging end extending from said handle, said bone engaging end adapted for engagement with the bearing surface, and wherein said bone engaging end includes at least one condyle shaped portion which includes a convexly curved bone contacting surface corresponding to a shape of the bearing surface, and wherein said convexly curved bone contacting surface extends longitudinally from said handle, said joint locator providing an indication of an orientation of the bearing surface.

32. The orthopaedic instrument system of claim 31, wherein said template includes an opening for slidingly receiving said joint locator, and wherein said template further includes a thumbscrew associated with said opening for locking said joint locator within said opening.

33. The orthopaedic instrument system of claim 31, wherein said template includes at least one hole therein, each said hole being sized to receive a corresponding fastener therein adapted for attaching said template to the bone.

34. The orthopaedic instrument system of claim 31, wherein the bearing surface is oriented relative to a longitudinal axis of the bone, said joint locator having a handle extending from said bone engaging end, said bone engaging end being configured and adapted to engage said bearing surface such that said handle is disposed at a corresponding orientation relative to the longitudinal axis and thereby provides an indication of the orientation of the bearing surface relative to the longitudinal axis.

* * * * *